United States Patent
Choi et al.

(10) Patent No.: US 9,529,100 B2
(45) Date of Patent: Dec. 27, 2016

(54) POSITRON EMISSION TOMOGRAPHY DETECTOR AND POSITRON EMISSION TOMOGRAPHY SYSTEM USING SAME

(71) Applicant: Sogang University Research Foundation, Seoul (KR)

(72) Inventors: Yong Choi, Seoul (KR); Hyeok Jun Choe, Gyeonggi-do (KR)

(73) Assignee: Sogang University Research Foundation (KR)

( * ) Notice: Subject to any disclaimer, the term of this patent is extended or adjusted under 35 U.S.C. 154(b) by 0 days.

(21) Appl. No.: 14/648,171

(22) PCT Filed: Dec. 31, 2013

(86) PCT No.: PCT/KR2013/012424
§ 371 (c)(1),
(2) Date: Aug. 18, 2015

(87) PCT Pub. No.: WO2014/193066
PCT Pub. Date: Dec. 4, 2014

(65) Prior Publication Data
US 2015/0378035 A1  Dec. 31, 2015

(30) Foreign Application Priority Data
May 27, 2013 (KR) ........................ 10-2013-0059804

(51) Int. Cl.
G01T 1/29 (2006.01)
A61B 6/03 (2006.01)
G01T 1/161 (2006.01)

(52) U.S. Cl.
CPC ............ *G01T 1/2985* (2013.01); *A61B 6/037* (2013.01); *G01T 1/161* (2013.01)

(58) Field of Classification Search
CPC .................................................. G01T 1/2985
See application file for complete search history.

(56) References Cited

U.S. PATENT DOCUMENTS 8,258,483 B1 * 9/2012 Boatner .................. G01T 1/201
250/367
2002/0148970 A1 10/2002 Wong et al.
(Continued)

FOREIGN PATENT DOCUMENTS

KR  2009 0057831 A  6/2009
KR  2010 0122596 A  11/2010
KR  10 1088057 B   11/2011

OTHER PUBLICATIONS

International Search Report from PCT/KR2013/012424 issued Apr. 25, 2014 (2 pgs).

*Primary Examiner* — Yara B Green
(74) *Attorney, Agent, or Firm* — Brinks Gilson & Lione

(57) ABSTRACT

The present disclosure relates to a positron emission tomography detector and a positron emission tomography system using the same. More particularly, the positron emission tomography detector includes: a lower detecting unit configured to have a plurality of detector modules disposed in a ring or polygonal shape; and an upper detecting unit configured to have a plurality of detector modules which are spaced apart from each other by a predetermined distance, or of which at least some are in contact with each other to be formed on the lower detecting unit, and formed in a conical shape which is tilted by a preset angle. By the configuration as described above, since the positron emission tomography detector and the positron emission tomography system using the same according to the present disclosure have a large number of effective lines of response (LOR) and increase geometric efficiency, it is possible to improve sensitivity.

9 Claims, 5 Drawing Sheets

(56) References Cited

U.S. PATENT DOCUMENTS

| | | | |
|---|---|---|---|
| 2008/0173819 A1* | 7/2008 | Grazioso | G01T 1/1603 250/363.05 |
| 2010/0006769 A1* | 1/2010 | Kraft | G01T 1/2907 250/370.11 |
| 2010/0108896 A1* | 5/2010 | Surti | G01T 1/00 250/363.04 |
| 2011/0024636 A1 | 2/2011 | Gagnon et al. | |
| 2011/0092814 A1* | 4/2011 | Yamaya | A61N 5/1048 600/427 |
| 2011/0263965 A1* | 10/2011 | Kang | G01T 1/2935 600/411 |
| 2012/0001064 A1* | 1/2012 | Bingham | G01T 1/2985 250/252.1 |
| 2012/0068076 A1* | 3/2012 | Daghighian | A61B 6/037 250/363.03 |
| 2012/0104263 A1* | 5/2012 | Gagnon | A61B 6/037 250/363.03 |
| 2012/0271164 A1* | 10/2012 | Gagnon | A61B 6/037 600/427 |

\* cited by examiner

POSITRON EMISSION TOMOGRAPHY DETECTOR AND POSITRON EMISSION TOMOGRAPHY SYSTEM USING SAME

CROSS-REFERENCE TO RELATED APPLICATION

This application is based on and claims the benefit of priority to Korean Patent Application No. 10-2013-0059804, filed on May 27, 2013 in the Korean Intellectual Property Office, the disclosure of which is incorporated herein in its entirety by reference.

TECHNICAL FIELD

The present disclosure relates to a positron emission tomography detector and a positron emission tomography system using the same, and more particularly, to a positron emission tomography detector capable of improving sensitivity and a positron emission tomography system using the same.

BACKGROUND

Recently, as an IT technology has been developed, medical imaging devices that non-invasively shows an interior of a body in an image form to provide information necessary to accurately diagnose diseases have been widely used. Among the above-mentioned medical imaging devices, examples of a tomography image obtainer include a computed tomography (CT), a magnetic resonance imaging (MRI), a nuclear medicine imaging device, and the like. Among these, the computed tomography (CT) and the magnetic resonance imaging (MRI) provide a detailed anatomical image of the body, and the nuclear medicine imaging device using a radioactive isotope provides an image showing a physiological phenomenon in the body.

Particularly, a positron emission tomography (PET) among the nuclear medicine imaging devices images an intra-body distribution of radioactive pharmaceuticals after injecting the radioactive pharmaceuticals emitting positron into the body which becomes a target of research and diagnosis through an intravenous injection or inhalation. The above-mentioned PET image is used as a tool that measures several physiopathological phenomena, and has an advantage capable of imaging concentration of neuroceptor and delivery, and gene as well as measuring biochemical phenomena such as a blood flow rate, a basal metabolic rate, and a synthesis rate.

In the positron emission tomography technology described above, spatial resolution and sensitivity are determined as the most important factors, wherein the spatial resolution means capability capable of spatially distinguishing radioactive sources which are adjacent to each other in the image obtained from the positron emission tomography. A decrease in the above-mentioned spatial resolution increases an image spread effect and causes a result that underestimates radioactive concentration of a small structure. Accordingly, examples of a method for improving spatial resolution include a use of scintillation crystal having a small size, a separate signal processing, improvement of an image reconstruction method, and the like.

In addition, sensitivity is an indicator indicating gamma rays detected by the PET among the gamma rays generated from the radioactive sources which are present within a field of view of a PET scanner. As main factors affecting on the above-mentioned sensitivity, there are a thickness of the scintillation crystal, a radius of a detector loop, and the like. In order to improve the above-mentioned sensitivity, a method using scintillation crystal having high stopping power and rapid decay time, a method for maximizing a solid angle coverage by reducing a size of a PET bore, a method for expanding an axial field of view, a method for minimizing dead time loss, etc., have been suggested.

Particularly, sensitivity in an axial direction of the PET system is highest at a center of an axis and is decreased toward an outer portion of the axis, and in this case, a problem occurs that a PET image obtained from the outer portion of the axis has decreased quality thereof.

In order to secure a field of view in the axial direction to solve the above-mentioned problem, a length of the axis is increased, and in this case, a problem occurs that overall costs of the system are increased.

A related art of the positron emission tomography detector and the positron emission tomography system using the same is as follows.

Related Art 1, which is Korean Patent No. 1088057 (registered on Nov. 23, 2011), relates to a detector module for a positron emission tomography (PET) and a positron emission tomography using the same. The detector module for a positron emission tomography according to Related Art 1 includes: a scintillation layer in which a plurality of rod type scintillators arranged to be in parallel to an axis direction of a detection ring are configured to be arranged in a pixel type of array and the pixel array in which the plurality of rod type scintillators are arranged is arranged so that a cross section of the detection ring in a radial direction forms a trapezoidal shape; a pair of light diffusing layers each connected to both ends of the scintillation layer to diffuse scintillation signals transferred from the respective scintillators configuring the scintillation layer; a pair of optical sensor arrays each connected to the pair of light diffusing layers to convert the scintillation signals transferred from the light diffusing layers into an electrical signal; and a pair of detection circuit unit each connected to the pair of optical sensor arrays to compare and analyze the electrical signals transferred from the optical sensor arrays through a preset detection algorithm and detect reaction positions of gamma rays within the scintillation layer, wherein the gamma rays emitted from a photographing region are incident through side portions of the plurality of rod type scintillators arranged to be in parallel to the axis direction of the detection ring.

SUMMARY

The present disclosure has been made to solve the above-mentioned problems occurring in the prior art while advantages achieved by the prior art are maintained intact.

An aspect of the present disclosure provides a positron emission tomography detector which may be manufactured at economical costs while having uniform and high sensitivity regardless of measurement positions, and a positron emission tomography system using the same.

According to an aspect of the present disclosure, a positron emission tomography detector includes: a lower detecting unit configured to have a plurality of detector modules disposed in a ring or polygonal shape; and an upper detecting unit configured to have a plurality of detector modules which are spaced apart from each other by a predetermined distance, or of which at least some are in contact with each other to be formed on the lower detecting unit, and formed in a conical shape which is tilted by a preset angle.

The detecting module of the upper detecting unit may have any one cross section of a circle, a triangle, a quadrangle, a pentagon, a hexagon, and a polygon.

The detector module may include: a scintillation layer in which a plurality of rod type scintillators are arranged; a light diffusing layer connected to the scintillation layer to diffuse scintillation signals transferred from the respective scintillators configuring the scintillation layer; an optical sensor array connected to the light diffusing layer to convert the scintillation signals transferred from the light diffusing layer into electrical signals; and a detection circuit unit connected to the optical sensor array to compare and analyze the electrical signals transferred from the optical sensor array through a preset detection algorithm and detect reaction positions of gamma rays within the scintillation layer.

The scintillator may be any one of bismuth germinate (BGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide (LaBr3), lutetium iodide (LuI3), gadolinium oxyorthosilicate (GSO), lutetium gadolinium oxyorthosilicate (LGSO), and lutetium aluminum garnet (LuAG).

The optical sensor array may be formed of a photomultiplier tube (PMT) or a solid-state photomultiplier.

The solid-state photomultiplier may include at least one of a silicon photomultiplier (SiPM), a multi-pixel photon counter (MPPC), CdZnTe (CZT), CdTe, an avalanche photo diode (APD), and a PIN diode.

The solid-state photomultiplier may include a silicon based or germanium based solid-state photomultiplier.

The detector module may include: a scintillation layer in which a plurality of rod type scintillators are arranged; an optical sensor array connected to the scintillation layer to convert scintillation signals transferred from the respective scintillators into electrical signals; and a detection circuit unit connected to the optical sensor array to compare and analyze the electrical signal through a preset detection algorithm and detect reaction positions of gamma rays within the scintillation layer.

According to another aspect of the present disclosure, a positron emission tomography system includes: a detector including a lower detecting unit configured to have a plurality of detector modules disposed in a ring or polygonal shape, and an upper detecting unit configured to have a plurality of detector modules which are spaced apart from each other by a predetermined distance, or of which at least some are in contact with each other to be formed on the lower detecting unit, and formed in a conical shape which is tilted by a preset angle.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

The present disclosure will be described in detail so as to be easily practiced by a person skilled in the art to which the present disclosure pertains with reference to exemplary embodiments and the accompanying drawings. However, the present disclosure may be modified in various different ways and is not limited to the exemplary embodiments described herein.

First, before, describing a positron emission tomography detector and a positron emission tomography system using the same, a positron emission tomography will be schematically described.

The positron emission tomography (PET) is a device representing spatial position information for a distribution in a body of a positron emission nuclide with an image by measuring a pair of gamma rays simultaneously generated by an electron-positron annihilation phenomenon with a detector using radioactive pharmaceutical in which a positron emitter is marked as a tracer.

The present disclosure relates to a detector detecting a pair of gamma rays in the positron emission tomography described above.

Hereinafter, the positron emission tomography detector according to the present disclosure will be described in detail with reference to FIG. 1.

Figure 1:
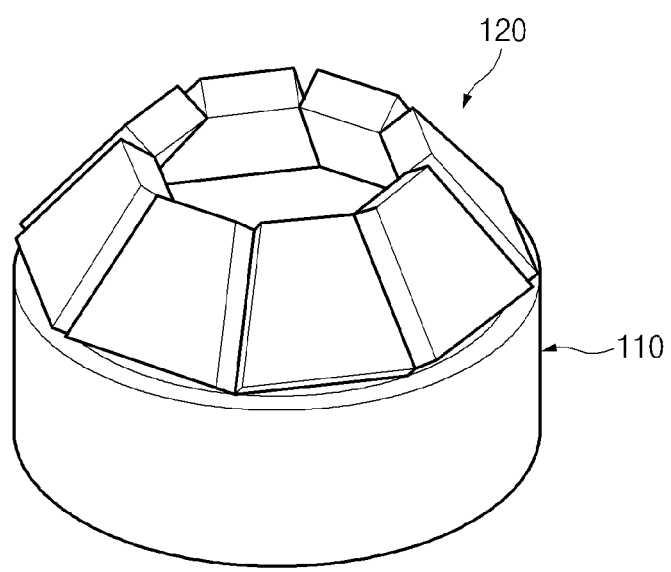
FIG. 1 is a perspective view of a positron emission tomography detector and a positron emission tomography system using the same according to an exemplary embodiment of the present disclosure.

FIG. 1 is a perspective view of the positron emission tomography detector according to an exemplary embodiment of the present disclosure.

As illustrated in FIG. 1, the positron emission tomography detector according to the present disclosure is generally divided into a lower detecting unit 110 and an upper detecting unit 120.

The lower detecting unit 110 has a plurality of detector modules formed to be opposite to each other in a ring or polygonal shape.

The upper detecting unit 120 has a plurality of detector modules which are spaced apart from each other by a predetermined distance, or of which at least some are in contact with each other, and is formed on the lower detecting unit 110, and in this case, the upper detecting unit 120 is formed in a conical shape which is inwardly tilted by a preset angle. In this case, the detector module of the upper detecting unit 120 may have any one cross section of a circle, a triangle, a quadrangle, a pentagon, a hexagon, and a polygon.

Particularly, the detector modules of the lower detecting unit 110 and the upper detecting unit 120 include a scintillation layer, a light diffusing layer, an optical sensor array, and a detection circuit unit.

The scintillation layer indicates a plurality of rod type scintillator arrays, and in this case, the scintillator may be made of at least one of bismuth germinate (BGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide (LaBr3), lutetium iodide (LuI3), gadolinium oxyorthosilicate (GSO), lutetium gadolinium oxyorthosilicate (LGSO), and lutetium aluminum garnet (LuAG).

The light diffusing layers are each connected to the scintillation layers to diffuse scintillation signals transferred from the respective scintillators configuring the scintillation layers. Here, the light diffusing layer may be made of quartz or flexible glass.

Here, the light diffusing layer may be omitted from the detector module. As such, in the case in which the light diffusing layer within the detector module is omitted, the scintillation signals transferred from the respective scintillators configuring the scintillation layers are transferred to the optical sensor array.

The optical sensor array is connected to the light diffusing layer to convert the scintillation signals transferred from the light diffusing layer into an electrical signal. Here, the optical sensor array may be formed of a photomultiplier tube (PMT), or may be formed of a solid-state photomultiplier such as a silicon photomultiplier (SiPM), a multi-pixel photon counter (MPPC), CdZnTe (CZT), CdTe, an avalanche photo diode (APD), a PIN diode, or the like. The above-mentioned solid-state photomultiplier may include a silicon based solid-state photomultiplier or a germanium based solid-state photomultiplier. As well, in the case in which the optical sensor array is formed of CdZnTe (CZT) or CdTe, the scintillator configuring the scintillation layer among the components of the detector module may be omitted.

The detection circuit units are each connected to the optical sensor array to compare and analyze the electrical signal transferred from the optical sensor array through a preset detection algorithm and detect reaction positions of gamma rays within the scintillation layer.

Figure 2:
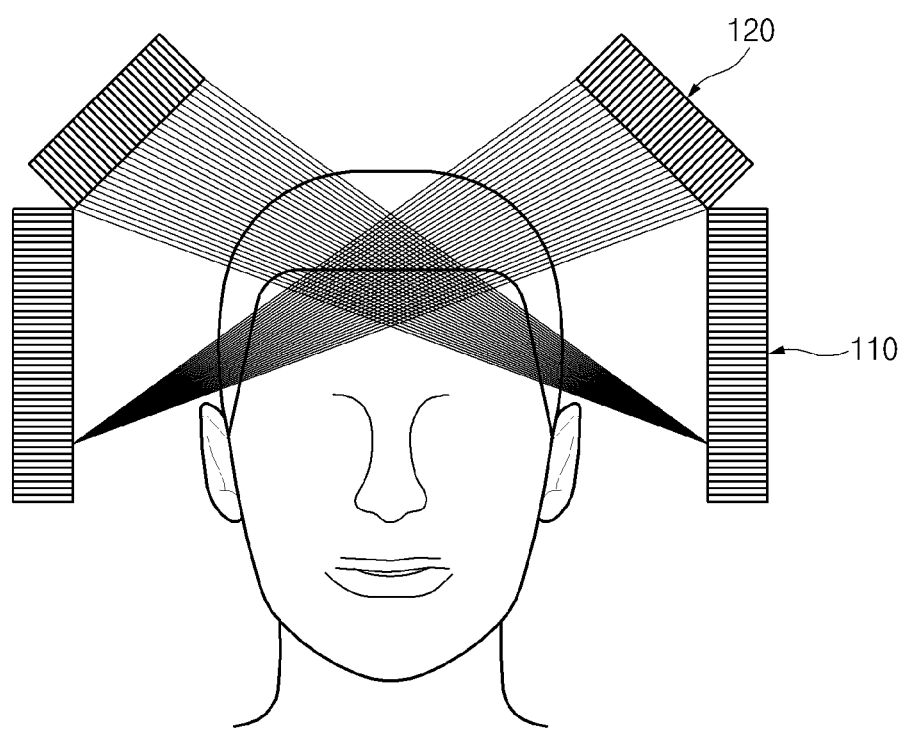
FIG. 2 is a diagram illustrating a figure detecting gamma rays emitted from a radioactive pharmaceutical distributed in a brain of a body using the positron emission tomography detector according to the present disclosure.

FIG. 2 is a diagram illustrating a figure detecting gamma rays emitted from a radioactive pharmaceutical distributed in a brain of a body using the positron emission tomography detector according to the present disclosure.

As illustrated in FIG. 2, since the positron emission tomography detector according to the present disclosure has the lower detecting unit 110 which is formed in a ring shape having a center of a hallow state, if a body portion to which a PET image is to be photographed, for example, a head of an examinee is positioned at the center of the hallow state, the lower detecting unit 110 of the ring or polygonal shape corresponds to both sides of the head and the upper detecting unit 120 disposed to be inwardly tilted by a predetermined angle corresponds to a side upper portion of the head. In this case, the angle that the upper detecting unit 120 is inwardly tilted may be adjusted by a head size of the examinee or a user.

As described above, since the number of axial effective lines of response (LOR) between the detector module of the upper detecting unit 120 having a predetermined tilted angle positioned at an upper side of the head and the detector module of the lower detecting unit 110 positioned at a position facing the detector module of the upper detecting unit 120 is increased, sensitivity may be very improved.

Particularly, the detector module of the upper detecting unit is disposed by adjusting the tilted angle thereof so that a transverse filed of view (FOV) is changed along an axis direction, thereby making it possible to very improve sensitivity. As well, as a tomographic image having high sensitivity is rapidly obtained, an examination time may also be significantly reduced.

Sensitivity of the detecting units according to the present disclosure and the related art will be described with reference to FIG. 3.

Figure 3:
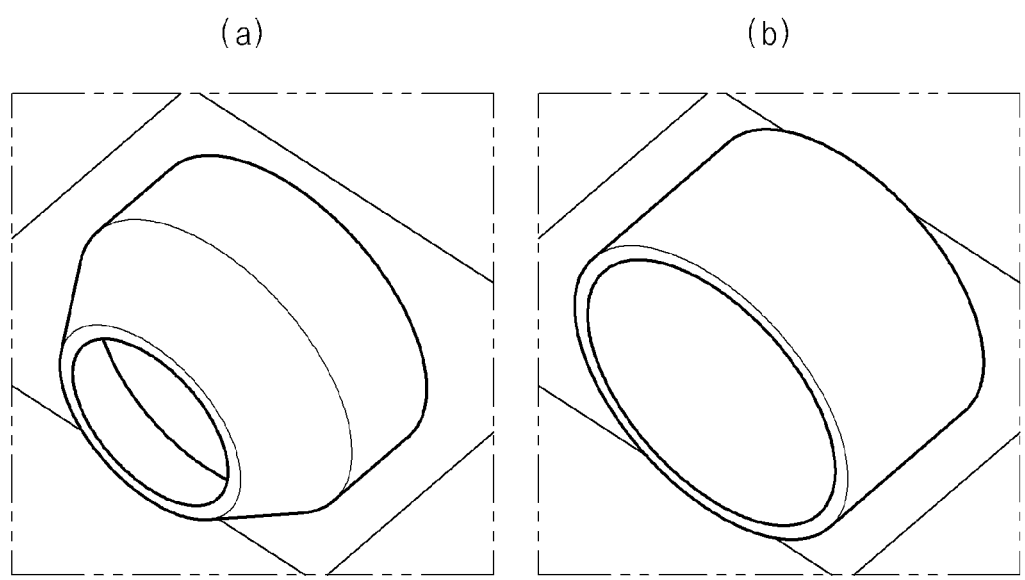
FIG. 3 is a diagram each illustrating detecting units according to the related art and the present disclosure.

FIG. 3 is a diagram each illustrating detecting units according to the related art and the present disclosure.

As illustrated in FIG. 3A, in the detecting unit according to the present disclosure, a detecting region has an area of 79,497 mm$^2$, a diameter of an uppermost portion of the detecting unit is 240 mm, and a diameter of a lowest portion thereof is 390 mm. An axis length of the lower detecting unit is 135 mm and an axis length of the upper detecting unit is 117 mm, of which a total length is 252 mm, and the tilted angle of the upper detecting unit is 60°. Unlike this, in the detecting unit according to the related art illustrated in FIG. 3B, the detecting region has an area of 79,497 mm$^2$, which is similar to the detecting unit according to the present disclosure, but a diameter of the detecting unit is 390 mm, an axis length is 246 mm, and since the detecting unit according to the related art is not tilted, an angle thereof is 90°.

In this case, the detecting units according to the present disclosure and the related art have a condition that a size of crystal forming the detector module is 3×3×20 mm$^2$.

The detecting units according to the present disclosure and the related art having the above-mentioned condition may each calculate sensitivity according to the following Equation 1.

$$\text{Geometric efficiency} = A/D \quad \text{[Equation 1]}$$

Here, A represents the axis length of the detecting unit and D represents the diameter of the detecting unit.

Figure 4:
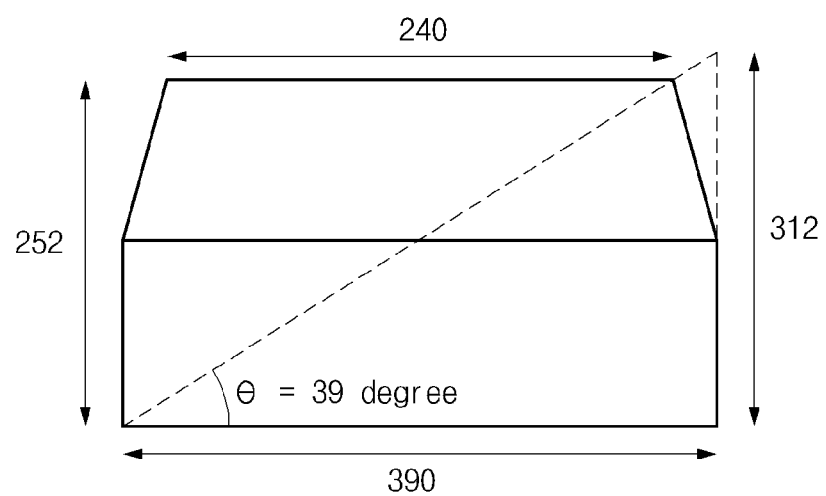
FIG. 4 is a diagram illustrating a solid angle calculation for the detecting unit according to the present disclosure.

Since it is difficult to reflect a geometric shape of the upper portion of the detecting unit according to the present disclosure which is tilted at the predetermined angle in applying Equation 1 to the calculation of sensitivity of the detecting unit according to the present disclosure as it is, the axis length of the detecting unit to which the geometric shape according to the present disclosure is reflected may be obtained on the assumption of FIG. 4. In order to obtain a line of response (LOR) corresponding to a solid angle of 39° when the detecting unit according to the related art has the diameter of the lowest portion of the detecting unit of 390 mm as in the present disclosure, the axis length needs to be 312 mm. That is, the detecting unit according to the present disclosure has the same sensitivity as that of the detecting unit according to the related art having the diameter of 390 mm and the axis length of 312 mm.

In accordance with the above-mentioned calculation method, it may be seen that the detecting unit according to the present disclosure has sensitivity which is improved as much as about 27% as compared to the detecting unit according to the related art.

In addition, as a simulation setting for calculating sensitivity of the detecting units according to the present disclosure and the related art, geant4 application for tomographic emission (GATE), which is one of monte carlo simulation tools, was used, an energy window was set to 410 to 613 keV, which is ±20% of 511 keV, and a time window was set to 10 ns.

In accordance with the above-mentioned simulation, it may be seen that the detecting unit according to the present disclosure has sensitivity which is improved as much as about 29% as compared to the detecting unit according to the related art.

Figure 5:
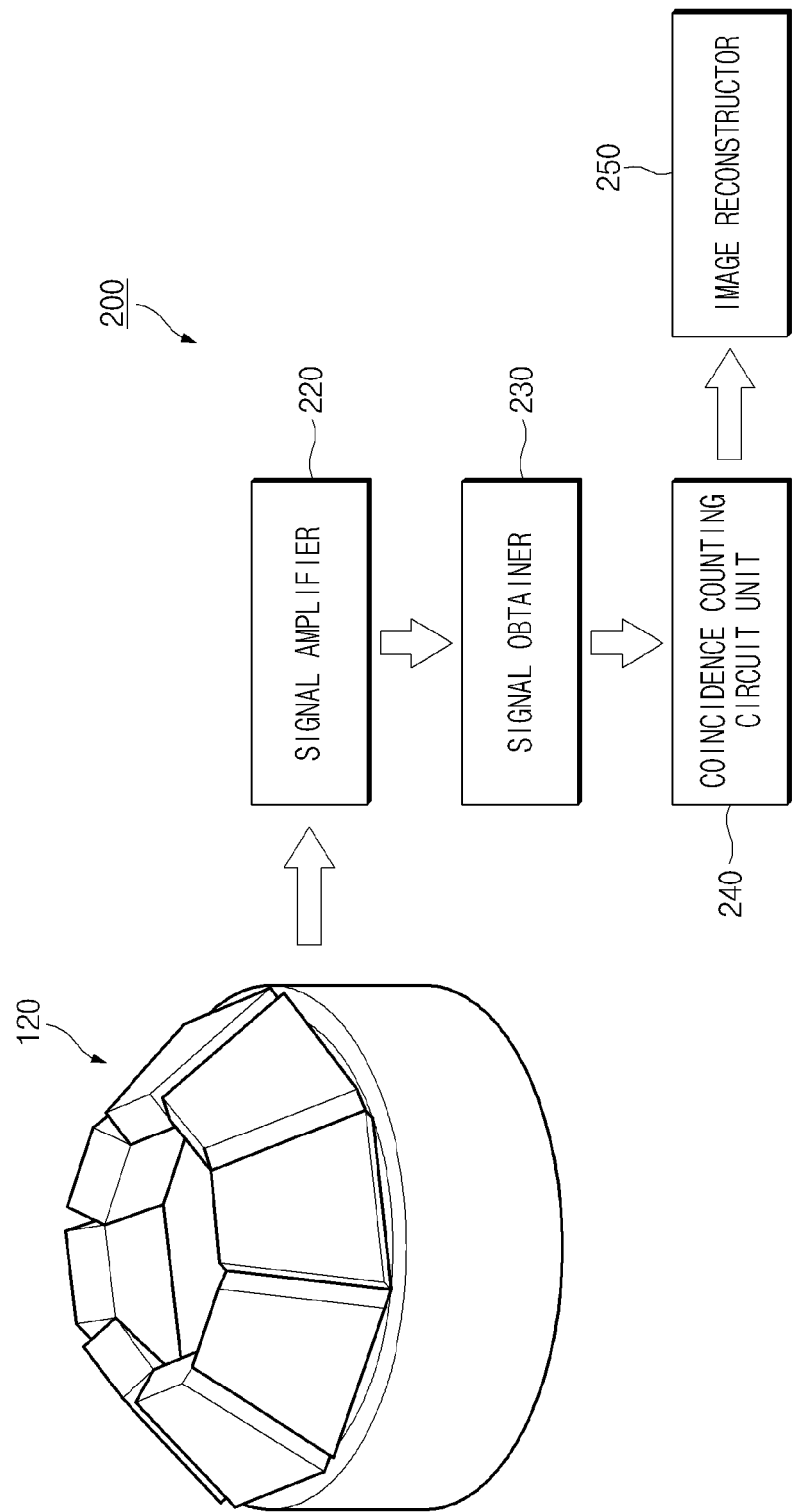
FIG. 5 is a diagram illustrating a structure of a positron emission tomography system using a positron emission tomography detector according to another exemplary embodiment of the present disclosure.

FIG. 5 is a diagram illustrating a structure of a positron emission tomography system using a positron emission tomography detector according to another exemplary embodiment of the present disclosure.

As illustrated in FIG. 5, the detector 210 described above with reference to FIG. 1 detects the gamma rays through the lower detecting unit formed in the ring or polygonal shape and the upper detecting unit formed in the conical shape which is tilted by the preset angle, converts the gamma rays into the scintillation signals, and then converts the scintillation signals into the electrical signals.

A signal amplifier 220 shapes and amplifies the converted electrical signals.

A signal obtainer 230 obtains a converted digital signal by sampling the amplified electrical signals.

A coincidence counting circuit unit 240 measures position information through the digital signal.

An image reconstructor 250 obtains a tomographic image containing 3D information for the body by analyzing and reconstructing the position information. The above-mentioned image reconstructor 250 reconstructs an image using methods such as projection and backprojection, filtered backprojection (FBP), maximum likelihood reconstruction, maximum a posteriori (MAP) reconstruction, and the like.

As described above, according to the exemplary embodiments of the present disclosure, since the positron emission tomography detector and the positron emission tomography system using the same have a large number of effective lines of response (LOR) and increase geometric efficiency, it is possible to improve sensitivity.

In addition, the positron emission tomography detector and the positron emission tomography system using the same according to the present disclosure may obtain relatively constant sensitivity regardless of the measurement position such as the center or the outer portion of the axis.

Further, since the positron emission tomography detector and the positron emission tomography system using the same do not require additional costs incurred as the length of the axis is increased in order to secure high sensitivity in the field of view in the axial direction, overall manufacturing costs may be reduced.

Hereinabove, although the exemplary embodiment of the present disclosure have been described, the present disclosure is not limited thereto, and various modifications are made without departing from the scope and spirit of the present disclosure, which is also within the following claims.

What is claimed is:

1. A positron emission tomography detector comprising:
a lower detecting unit configured to have a plurality of detector modules disposed in a ring or polygonal shape; and
an upper detecting unit configured to have a plurality of detector modules which are spaced apart from each other by a predetermined distance, or of which at least some are in contact with each other to be formed on the lower detecting unit, and formed in a conical shape which is tilted by a preset angle.

2. The positron emission tomography detector according to claim 1, wherein the detecting module of the upper detecting unit has any one cross section of a circle, a triangle, a quadrangle, a pentagon, a hexagon, and a polygon.

3. The positron emission tomography detector according to claim 1, wherein the detector module includes:

a scintillation layer in which a plurality of rod type scintillators are arranged;
a light diffusing layer connected to the scintillation layer to diffuse scintillation signals transferred from the respective scintillators configuring the scintillation layer;
an optical sensor array connected to the light diffusing layer to convert the scintillation signals transferred from the light diffusing layer into electrical signals; and
a detection circuit unit connected to the optical sensor array to compare and analyze the electrical signals transferred from the optical sensor array through a preset detection algorithm and detect reaction positions of gamma rays within the scintillation layer.

4. The positron emission tomography detector according to claim 3, wherein the scintillator is any one of bismuth germinate (BGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide (LaBr3), lutetium iodide (LuI3), gadolinium oxyorthosilicate (GSO), lutetium gadolinium oxyorthosilicate (LGSO), and lutetium aluminum garnet (LuAG).

5. The positron emission tomography detector according to claim 3, wherein the optical sensor array is formed of a photomultiplier tube (PMT) or a solid-state photomultiplier.

6. The positron emission tomography detector according to claim 5, wherein the solid-state photomultiplier includes at least one of a silicon photomultiplier (SiPM), a multi-pixel photon counter (MPPC), CdZnTe (CZT), CdTe, an avalanche photo diode (APD), and a PIN diode.

7. The positron emission tomography detector according to claim 5, wherein the solid-state photomultiplier includes a silicon based or germanium based solid-state photomultiplier.

8. The positron emission tomography detector according to claim 1, wherein the detector module includes:
a scintillation layer in which a plurality of rod type scintillators are arranged;
an optical sensor array connected to the scintillation layer to convert scintillation signals transferred from the respective scintillators into electrical signals; and
a detection circuit unit connected to the optical sensor array to compare and analyze the electrical signal through a preset detection algorithm and detect reaction positions of gamma rays within the scintillation layer.

9. A positron emission tomography system comprising:
a detector including a lower detecting unit configured to have a plurality of detector modules disposed in a ring or polygonal shape, and an upper detecting unit configured to have a plurality of detector modules which are spaced apart from each other by a predetermined distance, or of which at least some are in contact with each other to be formed on the lower detecting unit, and formed in a conical shape which is tilted by a preset angle.

* * * * *